US008284386B2

(12) United States Patent
Young et al.

(10) Patent No.: US 8,284,386 B2
(45) Date of Patent: Oct. 9, 2012

(54) SYSTEM AND METHOD FOR VERIFYING THE CONTENTS OF A FILLED, CAPPED PHARMACEUTICAL PRESCRIPTION

(75) Inventors: Demetris P. Young, Durham, NC (US); Richard D. Michelli, Raleigh, NC (US)

(73) Assignee: Parata Systems, LLC, Durham, NC (US)

( * ) Notice: Subject to any disclaimer, the term of this patent is extended or adjusted under 35 U.S.C. 154(b) by 485 days.

(21) Appl. No.: 12/623,917

(22) Filed: Nov. 23, 2009

(65) Prior Publication Data

US 2010/0131097 A1 May 27, 2010

Related U.S. Application Data

(60) Provisional application No. 61/118,006, filed on Nov. 26, 2008.

(51) Int. Cl.
*G01N 21/00* (2006.01)

(52) U.S. Cl. .......................................................... 356/72

(58) Field of Classification Search .................... 356/72; 700/244

See application file for complete search history.

(56) References Cited

U.S. PATENT DOCUMENTS 4,223,751 A 9/1980 Ayers et al.
4,695,163 A 9/1987 Schachar
5,337,902 A 8/1994 Evans et al.
5,337,919 A 8/1994 Spaulding et al.
5,504,332 A 4/1996 Richmond et al.
5,597,995 A 1/1997 Williams et al.
5,679,954 A 10/1997 Soloman
5,768,327 A 6/1998 Pinto et al.
5,770,864 A * 6/1998 Dlugos .................... 250/559.19
5,826,696 A 10/1998 Rupp et al.
5,884,806 A 3/1999 Boyer et al.
5,907,493 A 5/1999 Boyer et al.
5,960,098 A 9/1999 Tao
6,363,687 B1 4/2002 Luciano et al.
6,364,517 B1 4/2002 Yuyama et al.
6,471,088 B1 10/2002 Uema et al.

(Continued)

FOREIGN PATENT DOCUMENTS

DE 11 17 046 B 11/1961

(Continued)

OTHER PUBLICATIONS

Invitation to Pay Additional Fees dated Mar. 4, 2010 for PCT/US2009/065608.

(Continued)

*Primary Examiner* — Tarifur Chawdhury
*Assistant Examiner* — Abdullahi Nur
(74) *Attorney, Agent, or Firm* — Myers Bigel Sibley & Sajovec

(57) ABSTRACT

A system for verification of dispensed pharmaceuticals includes: a housing; a bar code scanning station mounted on the housing; a vision station mounted on the housing; a spectroscopy station mounted on the housing; an offloading station mounted on the housing; one or more conveyors mounted on the housing to convey pharmaceutical vials between the bar code scanning, vision, spectroscopy and offloading stations, and a controller associated with the bar code scanning, vision, spectroscopy and offloading stations and the conveyors to control their operations. A system of this configuration can use both vision and spectroscopy to verify the identity of the pharmaceutical in the container.

5 Claims, 14 Drawing Sheets

U.S. PATENT DOCUMENTS

| | | | | |
|---|---|---|---|---|
| 6,497,342 | B2 | 12/2002 | Zhang et al. | |
| 6,509,537 | B1 | 1/2003 | Krieg et al. | |
| 6,522,945 | B2 * | 2/2003 | Sleep et al. | 700/225 |
| 6,535,637 | B1 | 3/2003 | Wootton et al. | |
| 6,607,094 | B2 | 8/2003 | MacDonald | |
| 6,690,464 | B1 | 2/2004 | Lewis et al. | |
| 6,771,369 | B2 | 8/2004 | Rzasa et al. | |
| 6,919,556 | B1 | 7/2005 | Laurence | |
| 7,006,214 | B2 | 2/2006 | Rzasa et al. | |
| 7,028,723 | B1 | 4/2006 | Alouani et al. | |
| 7,080,755 | B2 | 7/2006 | Handfield et al. | |
| 7,099,741 | B2 | 8/2006 | Baranowski | |
| 7,139,639 | B2 | 11/2006 | Broussard et al. | |
| 7,218,395 | B2 | 5/2007 | Kaye et al. | |
| RE40,453 | E | 8/2008 | Lasher et al. | |
| 2003/0176942 | A1 | 9/2003 | Sleep et al. | |
| 2004/0004085 | A1 | 1/2004 | Williams et al. | |
| 2004/0104241 | A1 | 6/2004 | Broussard et al. | |
| 2004/0133705 | A1 | 7/2004 | Broussard et al. | |
| 2004/0207842 | A1 | 10/2004 | Rzasa et al. | |
| 2005/0004495 | A1 | 1/2005 | Goswami | |
| 2005/0288906 | A1 | 12/2005 | Drennen, III et al. | |
| 2006/0041330 | A1 | 2/2006 | Ansari et al. | |
| 2007/0008523 | A1 | 1/2007 | Kaye et al. | |
| 2007/0042346 | A1 | 2/2007 | Weiler, III | |
| 2007/0093932 | A1 | 4/2007 | Abdulhay et al. | |
| 2007/0150092 | A1 | 6/2007 | Ohmura et al. | |
| 2008/0061074 | A1 | 3/2008 | Remis et al. | |

FOREIGN PATENT DOCUMENTS

| | | | |
|---|---|---|---|
| DE | 11 80 317 | B | 10/1964 |
| DE | 195 01 650 | A1 | 7/1996 |
| EP | 0 452 905 | A1 | 10/1991 |
| EP | 0 656 200 | A2 | 6/1995 |
| FR | 2 726 651 | A1 | 5/1996 |
| JP | 03 214045 | A | 9/1991 |
| JP | 2004 226071 | A | 8/2004 |
| WO | WO 99/61324 | | 12/1999 |
| WO | WO 02/069897 | A2 | 9/2002 |
| WO | WO 2004/072868 | A1 | 8/2004 |
| WO | WO 2005/031302 | A2 | 4/2005 |
| WO | WO 2008/088729 | A1 | 7/2008 |

OTHER PUBLICATIONS

Aldridge et al., Identification of Tablet Formulations Inside Blister Packages by Near-Infrared Spectroscopy, 1994, vol. 48, No. 10, pp. 1272-1276, Applied Spectroscopy.

Alexander et al., New Technologies Forum 4: Process Measurement and Control, Date Unknown, pp. 1-18, royal Pharmaceutical Society.

Analyst, Application of Near-Infrared Reflectance Spectrometry to the Analytical Control of Pharmaceuticals: ranitidine Hydrochloride tablet Production, Feb. 1996, vol. 121, pp. 219-222, Analyst.

Andrew Smith, What Really Counts is Separation, Sep./Oct. 2002, pp. 82-88, Machinery Update.

Burns et al., NIR Analysis of Pharmaceuticals, 1992, vol. 13, pp. 549-563, Marcei Dekker, Inc., New York, New York, USA.

Choi et al., Spatially Resolved Broad-Band Dielectroscopy for Material Characterization, Jan. 30, 2001, pp. 1-11, Chemical & Fuels Engineering, University of Utah.

Chris Frank, Raman Analysis in Pharmaceuticals, Sep. 1998, pp. 1-4, Raman Review.

PCT International Search Report for PCT/US05/42342.

Dempster et al., Near-Infrared Methods for the Identification of Tablets in Clinical Trial Supplies, 1993, vol. 11, No. 11/12, pp. 1087-1092, Journal of Pharmaceutical & Biomedical Analysis.

Demptser et al., A Near-Infrared Reflectance Analysis Method for the Noninvasive Identification of Film-Coated and Non-Film Coated, Blister-Packed Tablets, 1995, pp. 43-61, Analytica Chimica Acta 310.

James K, Drennen and Robert A. Lodder, Nondestructive Near-Infrared Analysis of Intact Tablets for Determination of Degradation Products, Jul. 1990, vol. 79, No. 7, pp. 622-627, Journal of Pharmaceutical Sciences.

Journal of Pharmaceutical Sciences, Near-Infrared Spectroscopy and Imaging for the Monitoring of Powder Blend Homogeneity, Journal, Sep. 2001, vol. 90, No. 9, pp. 1298-1307, Journal of Pharmaceutical Sciences.

Kohn et al., Identification of Drugs by Near Infrared Spectra, 1992, vol. 37, No. 1, pp. 35-41, Journal of Forensic Sciences.

Lodder et al., Detection of Capsule Tampering by Near-Infrared Reflectance Analysis, Aug. 1, 1987, pp. 1921-1930, vol. 59, No. 15, American Chemical Society.

MacDonald et al., Some Applications of Near-Infrared Reflectance Analysis in the Pharmaceutical Industry, 1993, vol. 11, No. 11/12, pp. 1077-1085, Journal of Pharmaceutical & Biomedical Analysis.

Medical News Today, US Patent issued for Unique Prescription Verification Solution, Aug. 13, 2004, p. 1 of 1, Medical News Today.

Morisseau et al., Pharmaceutical Uses of Near-Infrared Spectroscopy, 1995, pp. 1071-1090, Drug Development and Industrial Pharmacy.

Nova Packaging Systems, New SV2 Intellisense, Retrieved Nov. 17, 2004 from Internet Site http://pei2004.packexpo.com/pei20004/packaging_supp:iers/ve/37054/pr_63.html , p. 1 of 1, Nova Packaging Systems.

P.A. Hailey, The Role of NIR Spectroscopy in the Measurement of Pharmaceutical Manufacture, Retrieved Oct. 27, 2005 from Internet Site http://www.brimrose.com/hailey.html, pp. 1-6, Brimrose.

Packaging Digest, Diverse Filling Line is Flexible and Fast, Retrieved oct. 16,2 011 from Internet Site http://www.packagingdigest.com/article/print/341813-Diverse_filling_line_is_flexible_and_fast.php Packaging Digest.

PACKWORLD.COM, Automated Tablet Packing, New Line Helps repackaging pay Off, Retrieved Oct. 25, 2005 from Internet Site http://www.packworld.com/cds_print.html?rec_id=12789, pp. 1-4, packworld.com.

PACKWORLD.COM, Electrostatic Sensing, retrieved Oct. 25, 2005 from Internet Site http://www.packworld.com/cds_print.html?rec_id=12621 p. 1 of 1, Packworld.com.

Parmeter et al., Guide for the Selection of Drug Detectors for Law Enforcement Applications NIJ guide 601-00, Aug. 2000, 64 pages, National Institute of Justice.

Pat Reynolds, Electrostaticosensing, Retrieved Nov. 17, 2004 from Internet Site http://www.dtindustries.com/packaging/packworldstory.asp_page_1_of_1, DT Packaging Systems Industries.

Pharmaceutical Analytical Sciences Group, Guidelines for the Development and Validation of Near Infrared (NIR) Spectroscopic Methods, Oct. 2001 pp. 1-41, Pharmaceutical Analytical Sciences Group.

Polli et al., Technology Vs Fake Drgs, retrieved Oct. 27, 2005 from Internet Site http://www.uspharmacist.com/index.asp?show=article&page=8_120.htm pp. 1-2, U.S. Pharmacist.

Presearch Limited, Technical Note N-DT-01 Statistical Analysis, Oct. 2002, pp. 1-5, Presearch Limited.

Spectrolab Life Sciences, DASI—A Unique Hand Carried Analyser for Drug Identification & Molecular Analysis, Date Unknown, p. 1 of 1, Spectrolab Life Sciences, Internet Site www.spectrolab.co.uk.

Supplernental European Search Report for EP 05 82 5091 dated Aug. 27, 2010.

Tony Lam, A New Era in Affordable Raman Spectroscopy, Jun. 2004, pp. 30-36, Raman Technology for Today's Spectroscopists.

Wu at al., Spectral Transformation and Wavelength Selection in near-infrared Spectra Classification, 1995 pp. 248-255, Analytica Chimica Acta 315.

The International Search Report and The Written Opinion for PCT/US2009/065808, mailed May 3, 2010.

The International Preliminary Report for PCT/US2009/065608, mailed Jun. 9, 2011.

* cited by examiner

SYSTEM AND METHOD FOR VERIFYING THE CONTENTS OF A FILLED, CAPPED PHARMACEUTICAL PRESCRIPTION

RELATED APPLICATION

This application claims priority from U.S. Provisional Patent Application No. 61/118,006, filed Nov. 26, 2008, the disclosure of which is hereby incorporated herein in its entirety.

FIELD OF THE INVENTION

The present invention is directed generally to the identification of pharmaceuticals, and more particularly to the automatic identification of dispensed pharmaceuticals.

BACKGROUND OF THE INVENTION

There is an ongoing and predicted long-term shortage of licensed pharmacists. Due to the increasing age of the population and the ever-increasing number of prescription medicines available, the demand for prescription drugs is growing at a rate that will far exceed the capacity and numbers of licensed pharmacists. The net impact of this imbalance is that pharmacists are increasingly spending more time doing clerical and administrative tasks such as verifying filled prescriptions and checking data entry done by pharmacy technicians. Since the capacity of any one pharmacist is fixed, the output of a pharmacy has become constrained. Consequently, the labor and total cost per prescription continues to rise. The December 2000 Department of Health and Human Services Report to Congress titled "The Pharmacist Workforce: A Study of the Supply and Demand for Pharmacists", which is hereby incorporated herein by reference, provides an overview of the above problem.

Due to these increased demands on a pharmacist's time, and the resulting increased reliance on technicians and other non-professional staff to fill prescriptions, there is an increased chance for prescription error. While these errors may take many forms, the likelihood of a dangerous or life-threatening "adverse drug event" increases proportionally with the increased chance of prescription fill error. Several studies have shown that prescription error rates are consistently in the 2% to 7% range, with a 4% error rate often cited as a reliable average. The number of deaths due to medication errors is estimated to exceed 7,000 per year in the United States alone. Of course, this number does not include non-fatal conditions from drugs that also result in some form of trauma or injury. The resulting litigation costs associated with these prescription fill errors have also dramatically increased.

Many existing pharmacy filling systems and procedures still require a human operator, whether that operator is a technician or a licensed pharmacist, to validate visually whether the drug that is delivered to the customer is correct. Thus, the human factor can contribute to the majority of prescription fill errors. Existing visual verification techniques rely on comparing an electronic image of the prescribed medication, i.e., a picture of the prescribed medication retrieved from a data library, with the actual medication that is dispensed for the patient. Other systems and procedures rely on comparing the dispensed medication with that in the original manufacturer's supply container, or comparing an electronic image of the filled prescription with an electronic image of the prescribed medication retrieved from a data library.

Each of these verification systems presents similar problems. First, these known verification methods assume that all drugs are visually distinct. This assumption causes many problems because many drugs are not, in fact, visually distinct and, in other cases, the visual differences between drugs is very subtle. For instance, manufacturers are rapidly running out of unique shapes, colors and sizes for their solid dosage form products. To further complicate the problem, generic drug manufactures may be using shapes, colors, and sizes that are different than that of the original manufacturer. Second, even though some known systems may utilize a National Drug Code (NDC) bar code to verify that the supply bottle being accessed corresponds correctly to the patient's prescription, a fraction of filled prescriptions are never picked up and may be returned to the supply shelves for reuse in later prescriptions. Because these reused bottles will not have a manufacturer's bar code on them, it is therefore difficult, if not impossible, to incorporate such validation schemes for these unused prescriptions. Furthermore, in these circumstances, a supply bottle is not available for a visual comparison with the filled prescription. Finally, each of these known manual verification and validation techniques typically requires that the pharmacist spend a significant portion of his day performing these administrative or clerical tasks and allows less time for patient consultation and other professional pharmacist activities.

Solid dosage pharmaceuticals (e.g., pills, tablets, and capsules) each have a unique chemical composition associated with them. This is often referred to as a chemical signature or fingerprint. Pharmaceuticals with varying dosage levels of the same active ingredient may have unique chemical signatures as well. Even slight variations in the active ingredient typically produce a unique chemical signature. In that regard, most pharmaceuticals can be identified accurately by the use of some form of chemical analysis. This same methodology may be applied to other forms of medication (e.g., liquids, creams, and powders). Particularly with solid dosage pharmaceutical products, while a group or package of products may look identical in the visible portion of the spectrum, each product may have a unique chemical signature in the near-infrared wavelength range (800 to 2500 nm). For example, U.S. Pat. No. 6,771,369 to Rzasa et al. describes a pharmaceutical discrimination system that relies on NIR for scanning the contents of a pharmaceutical vial. As another example, U.S. Pat. No. 7,218,395 to Kaye et al. describes the use of Raman spectroscopy for scanning vial contents. As a further example, co-assigned and co-pending U.S. patent application Ser. No. 11/972,849, filed Jan. 11, 2008, discusses a system that scans through the bottom end of the vial as the vial is capped. The disclosures of these patents are hereby incorporated herein in their entireties.

It may be desirable to enhance the reliability and precision of systems that employ spectroscopic verification of pharmaceuticals within vials.

SUMMARY OF THE INVENTION

As a first aspect, embodiments of the present invention are directed to a system for verification of dispensed pharmaceuticals. The system comprises: a housing; a bar code scanning station mounted on the housing; a vision station mounted on the housing; a spectroscopy station mounted on the housing; an offloading station mounted on the housing; one or more conveyors mounted on the housing to convey pharmaceutical vials between the bar code scanning, vision, spectroscopy and offloading stations, and a controller associated with the bar code scanning, vision, spectroscopy and offloading stations and the conveyors to control their operations. A system of this configuration can use both vision and spectroscopy to verify the identity of the pharmaceutical in the container.

As a second aspect, embodiments of the present invention are directed to a method of verifying the identity of dispensed pharmaceuticals. The method comprises the steps of: (a) scanning a bar code on a vial to determine an expected identity of a pharmaceutical in the vial; (b) conveying the vial to a vision station; (c) obtaining an image of the pharmaceutical within the vial at the vision station; (d) conveying the vial to a spectroscopy station; (e) obtaining a spectrum of the pharmaceutical within the vial; (f) determining whether the identity of the pharmaceutical in the vial matches the expected identity based on the image and/or the spectrum obtained in steps (c) and (e); and (g) conveying the vial to an offloading station.

As a third aspect, embodiments of the present invention are directed to a chamber for conducting spectroscopic scanning of objects within a container, comprising: an enclosure comprising a ceiling, side walls and a floor, wherein the floor includes a scanning aperture, and wherein the floor is inclined; a scanning device mounted below the floor for scanning objects in a container residing on the floor, the scanning device positioned to scan through the aperture; and positioning structure mounted within the enclosure to maintain the container in a selected position for scanning.

As a fourth aspect, embodiments of the present invention are directed to an apparatus for scanning a bar code on an object, comprising: a base panel; a conveyor mounted to the base panel and configured to convey the object in either of two opposing directions along a path; a turntable mounted on the panel and positioned at one end of the path to provide a scanning location; a drive unit associated with the turntable to rotate the turntable at the scanning location; and a bar code scanner oriented to scan a bar code on the object as it resides on the turntable.

As a fifth aspect, embodiments of the present invention are directed to an apparatus for offloading objects into two groups, comprising: a base; a turntable rotatably mounted in the base for rotation about an axis of rotation; a power unit associated with the turntable for rotating the turntable about the axis of rotation; an outer guide wall that follows generally a portion of the perimeter of the turntable; an inner guide wall that is generally parallel with the outer guide wall, the inner guide wall being positioned between the axis of rotation and the outer guide wall, the inner guide wall and the outer guide wall together defining a travel path; and a gate located in one of the inner guide wall and the outer guide wall, the gate moveable between a first position, in which the travel path is uninterrupted, and a second position, in which the gate interrupts the travel path and forces an object traveling on the travel path to veer to an exception area on the base. A collection area on the turntable is at least partially defined by the inner guide wall.

As a sixth aspect, embodiments of the present invention are directed to a method of confirming the identity of the contents of pharmaceutical vials, comprising the steps of: (a) scanning a bar code on a first vial to determine the expected contents of the first vial; (b) conveying the first vial to a vision station; (c) acquiring an image of the contents of the first vial at the vision station; (d) scanning a bar code on a second vial to determine the expected contents of the second vial; (e) conveying the first vial to a spectroscopy station; (f) conveying the second vial to the vision station; (g) acquiring an image of the contents of the second vial at the vision station; (h) acquiring a spectrum of the contents of the first vial at the spectroscopy station; (i) scanning a bar code on a third vial to determine the expected contents of the third vial; (j) conveying the first vial to an approval station; (k) conveying the second vial to the spectroscopy station; (l) conveying the third vial to the vision station; (m) acquiring an image of the contents of the third vial at the vision station; (n) acquiring a spectrum of the contents of the second vial at the spectroscopy station; (o) determining, based on at least one of steps (c) and (h), whether the contents of the first vial match the expected contents of the first vial and, if so, affixing indicia of approval on the first vial at the approval station; (p) scanning a bar code on a fourth vial to determine the expected contents of the fourth vial; (q) conveying the first vial to an offload station; (r) conveying the second vial to the approval station; (s) conveying the third vial to the spectroscopy station; and (t) conveying the fourth vial to the vision station.

DETAILED DESCRIPTION OF EMBODIMENTS OF THE INVENTION

Figure 1:
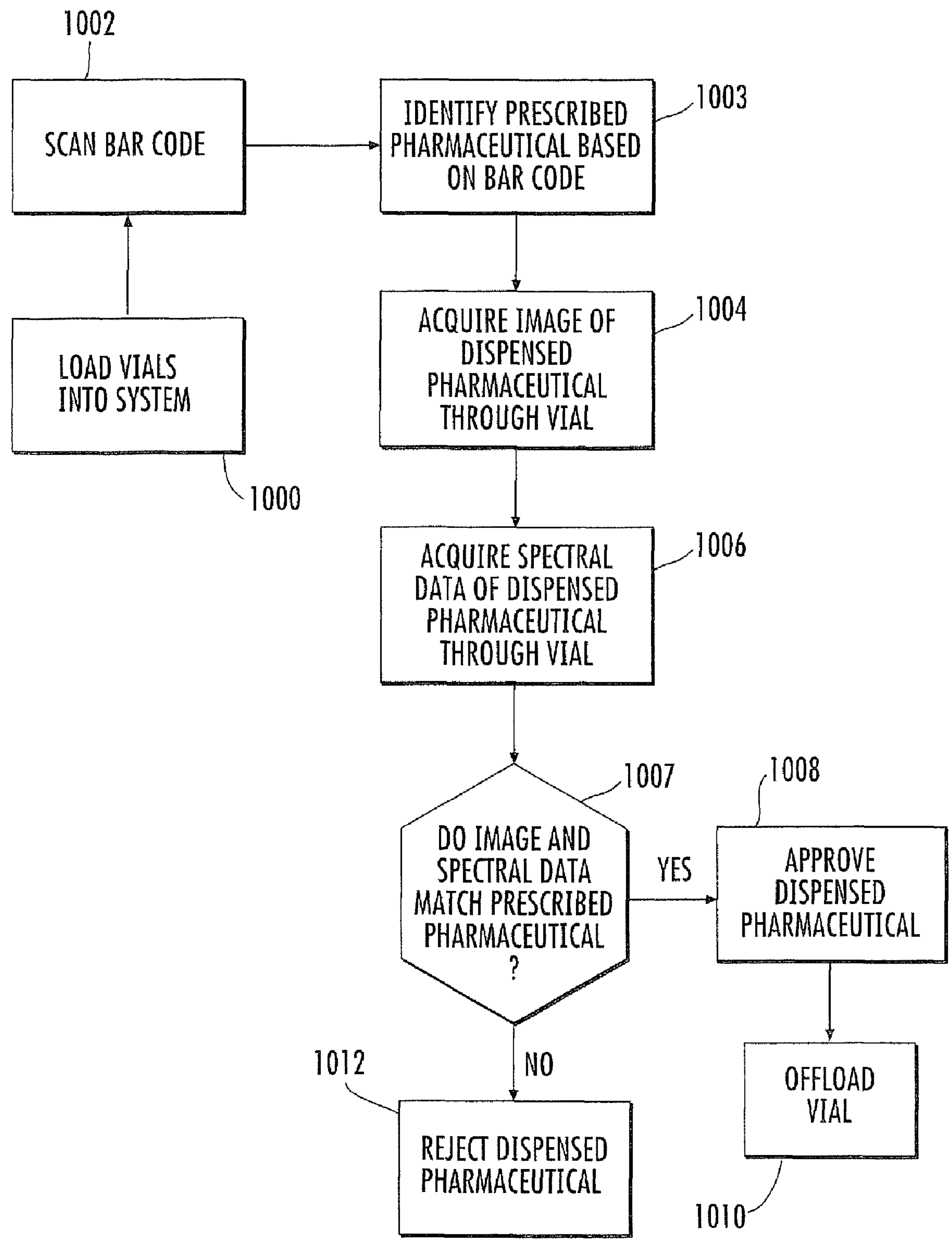
FIG. 1 is a flow chart illustrating operations of a pharmaceutical verification system according to embodiments of the present invention.

The present invention will now be described more fully hereinafter, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout. Thicknesses and dimensions of some components may be exaggerated for clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the expression "and/or" includes any and all combinations of one or more of the associated listed items.

In addition, spatially relative terms, such as "under", "below", "lower", "over", "upper," "front," "rear" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Well-known functions or constructions may not be described in detail for brevity and/or clarity.

Turning now to the drawings, embodiments of the present invention are directed to an automated system and/or method for verifying the identity of a dispensed pharmaceutical in a pharmaceutical vial (FIG. 1). As a first step, vials are loaded into the system for verification (Block 1000). The bar code on the label of each vial is then scanned (Block 1002) to identify the drug called for by the prescription (hereinafter the "prescribed pharmaceutical")(Block 1003). The vial is then scanned by a vision system for a comparison of the drug inside the vial (hereinafter the "dispensed pharmaceutical") and an image or other visual representation of the drug identified by the bar code (Block 1004). The vial is then subjected to spectroscopic analysis, with the spectrum generated for the dispensed pharmaceutical being compared to a known spectrum for identification purposes (Block 1006). If the identities of the prescribed pharmaceutical and the dispensed pharmaceutical match (Block 1007), the vial is stamped as approved (Block 1008) and offloaded for subsequent pick-up (Block 1010). If the identities do not match, the vial is rejected (Block 1012).

Figure 2:
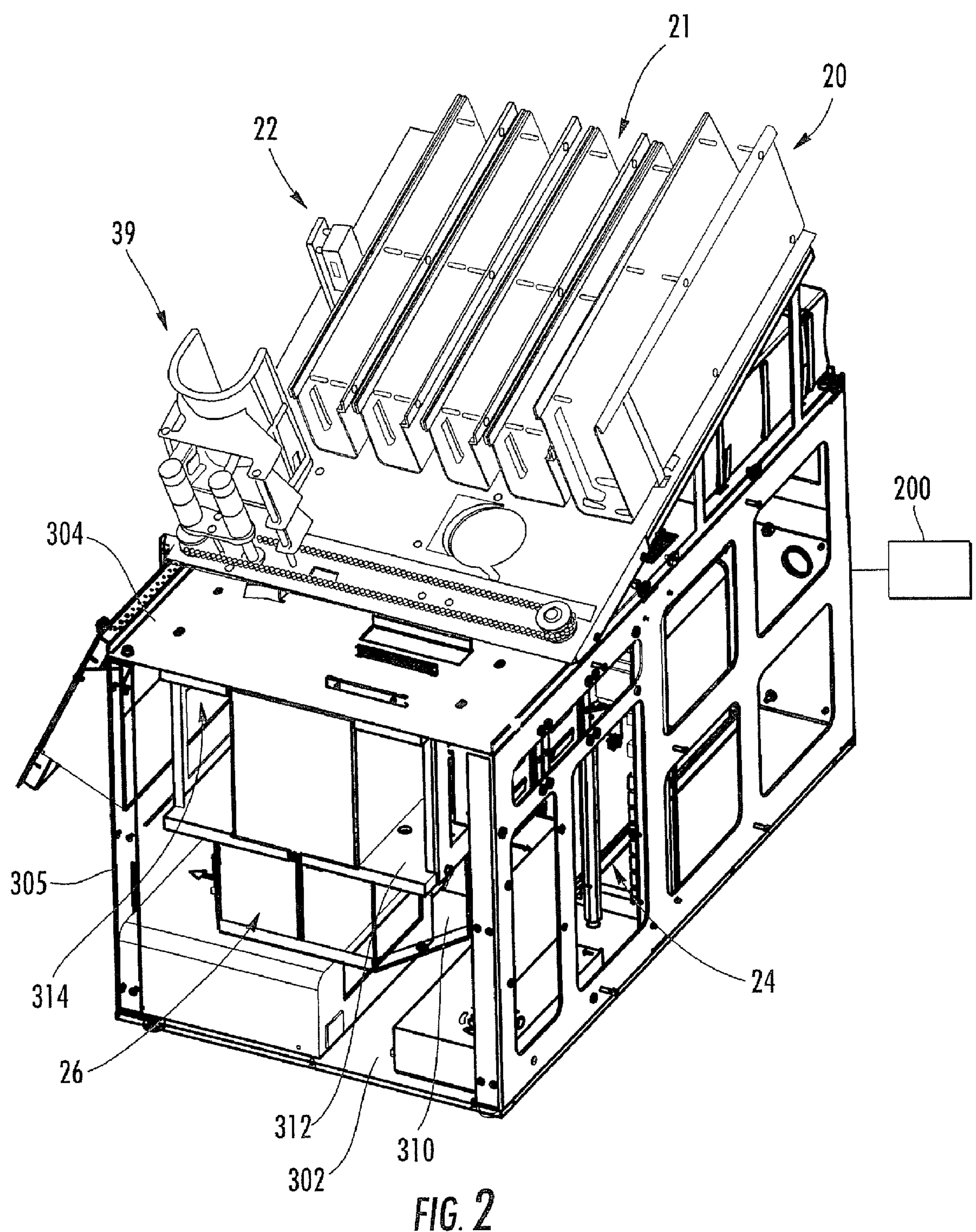
FIG. 2 is a front right perspective view of a pharmaceutical verification system according to embodiments of the present invention, with the side walls and end walls removed.
Figure 3:
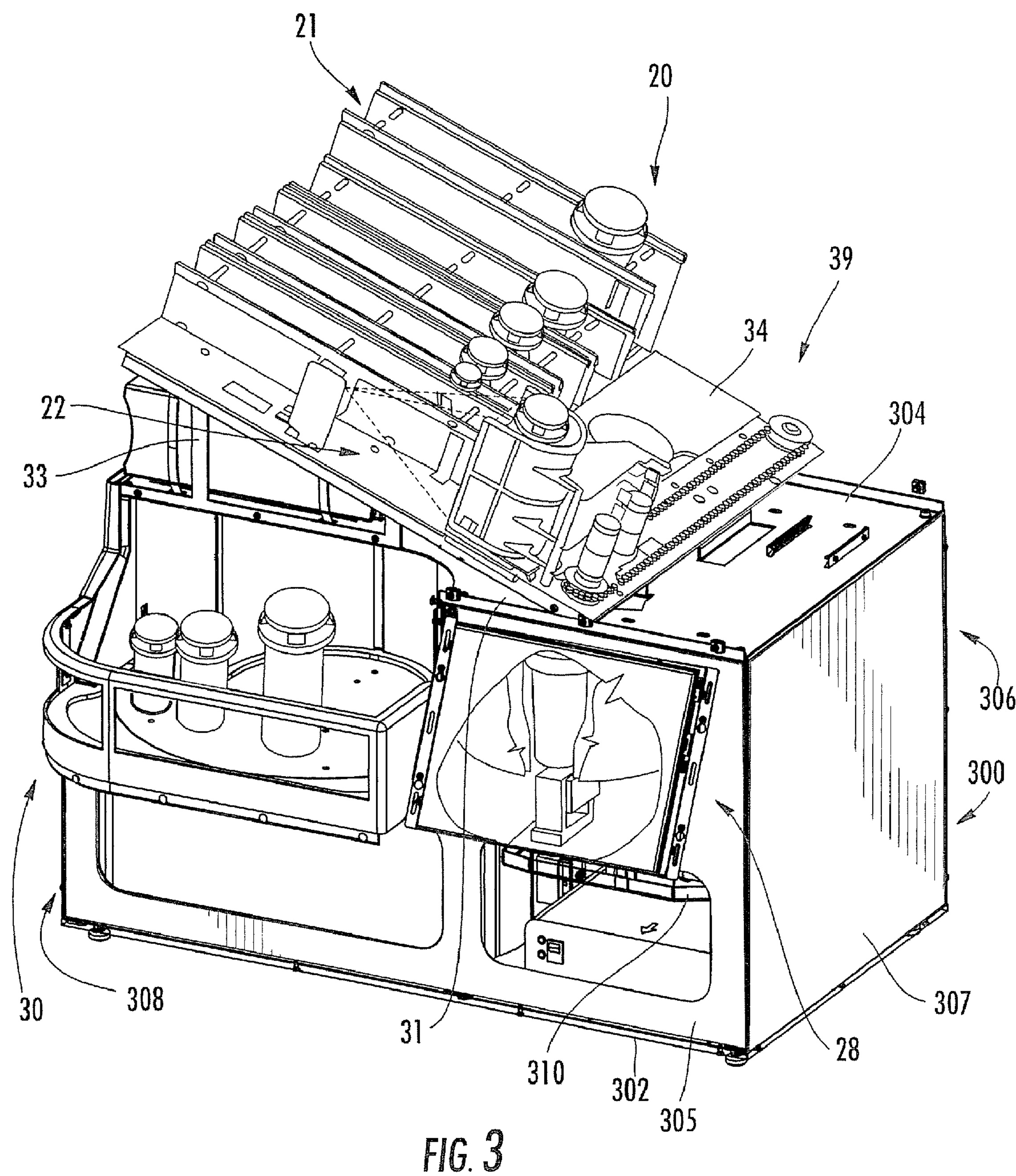
FIG. 3 is a front left perspective view of the pharmaceutical verification system of FIG. 2.
Figure 7:
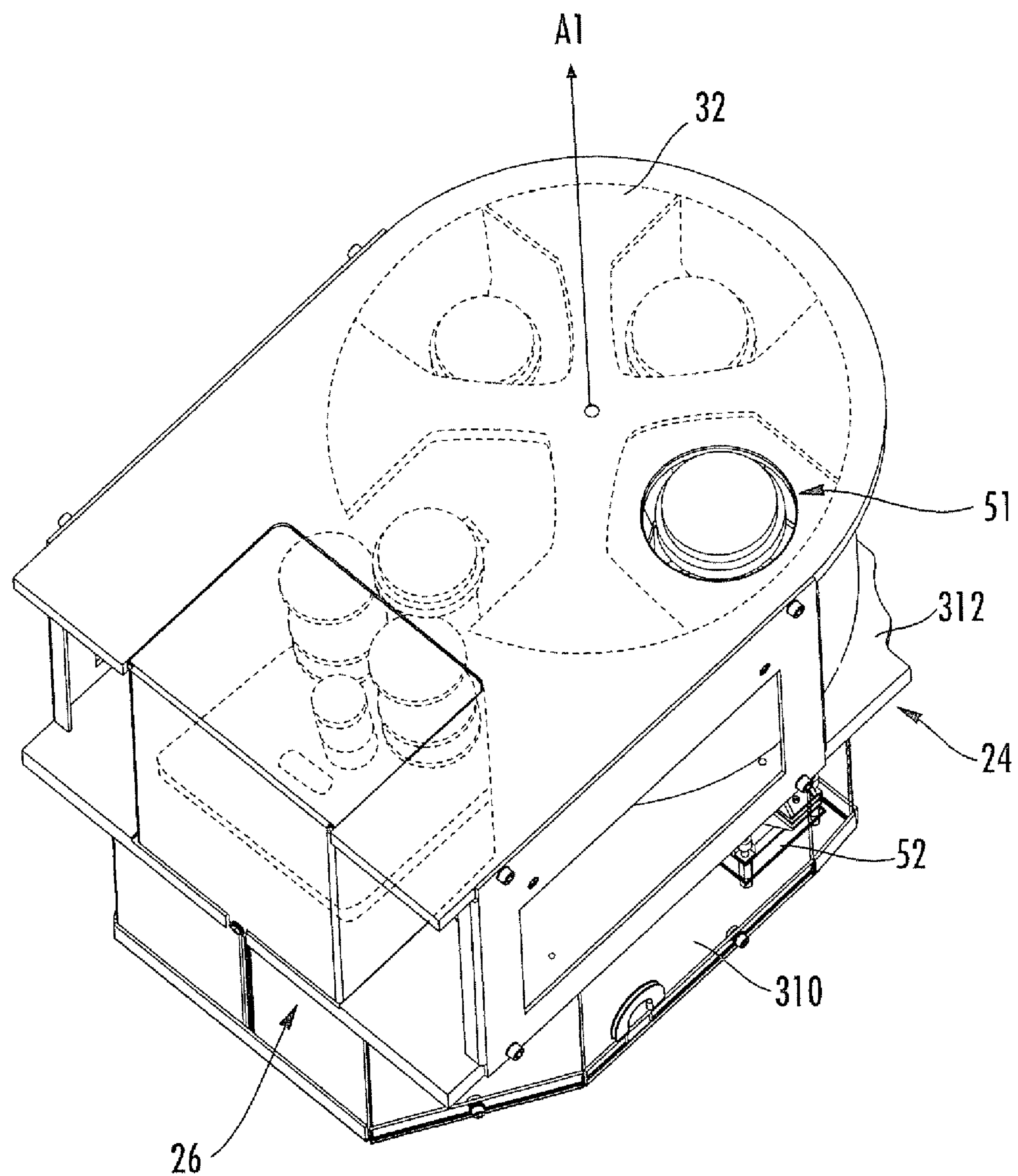
FIG. 7 is a top front perspective view of the wheel conveyor and the vision and spectroscopy stations of the pharmaceutical verification system of FIG. 2 with the housing removed.
Figure 8:
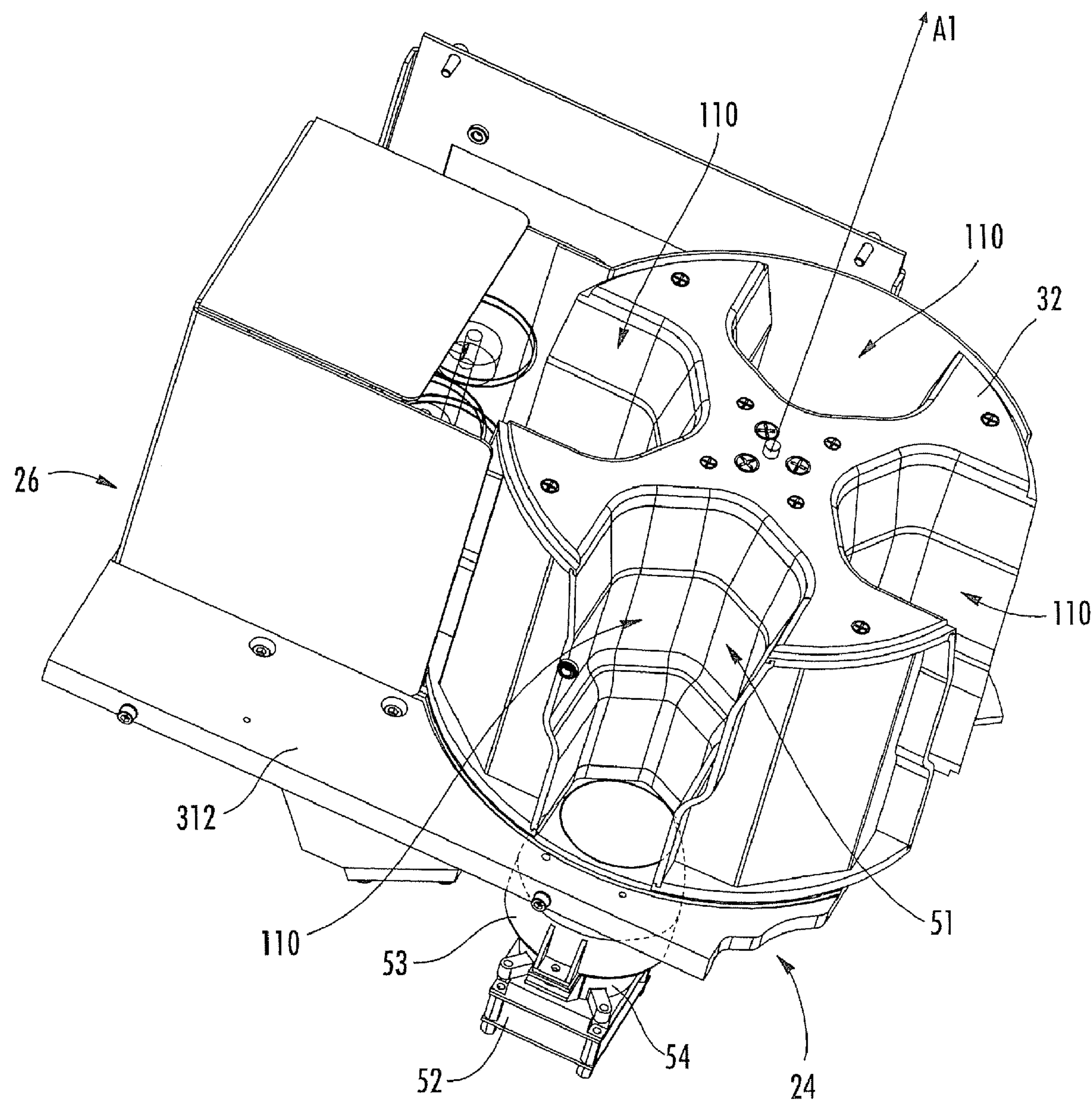
FIG. 8 is a rear top perspective view of the wheel conveyor and the vision, spectroscopy, and stamping stations of the pharmaceutical verification system of FIG. 2, with the housing and upper shelf removed.

Turning now to the drawings, a pharmaceutical verification system, designated broadly at 20, is shown in FIGS. 2 and 3. The system 20 includes a vial loading station 21, a bar code scanning station 22, a vision station 24, a spectroscopy station 26, a stamping station 28, and an offload station 30. Vials are moved between these stations with a sliding conveyor 39 (FIGS. 4 and 5) and a wheel conveyor 32 (FIGS. 7 and 8). A controller 200 controls the operation of the various stations, the sliding conveyor 39 and the wheel conveyor 32. These components will be described in greater detail below. The components are mounted in a housing 300, which includes a floor 302, a ceiling 304, side walls 305, 306, and end walls 307, 308. These panels form a generally box-shaped housing. Shelves 310, 312, 314 are positioned between the floor 302 and the ceiling 304 and serve as mounting locations for some of the components of the various stations.

Figure 4:
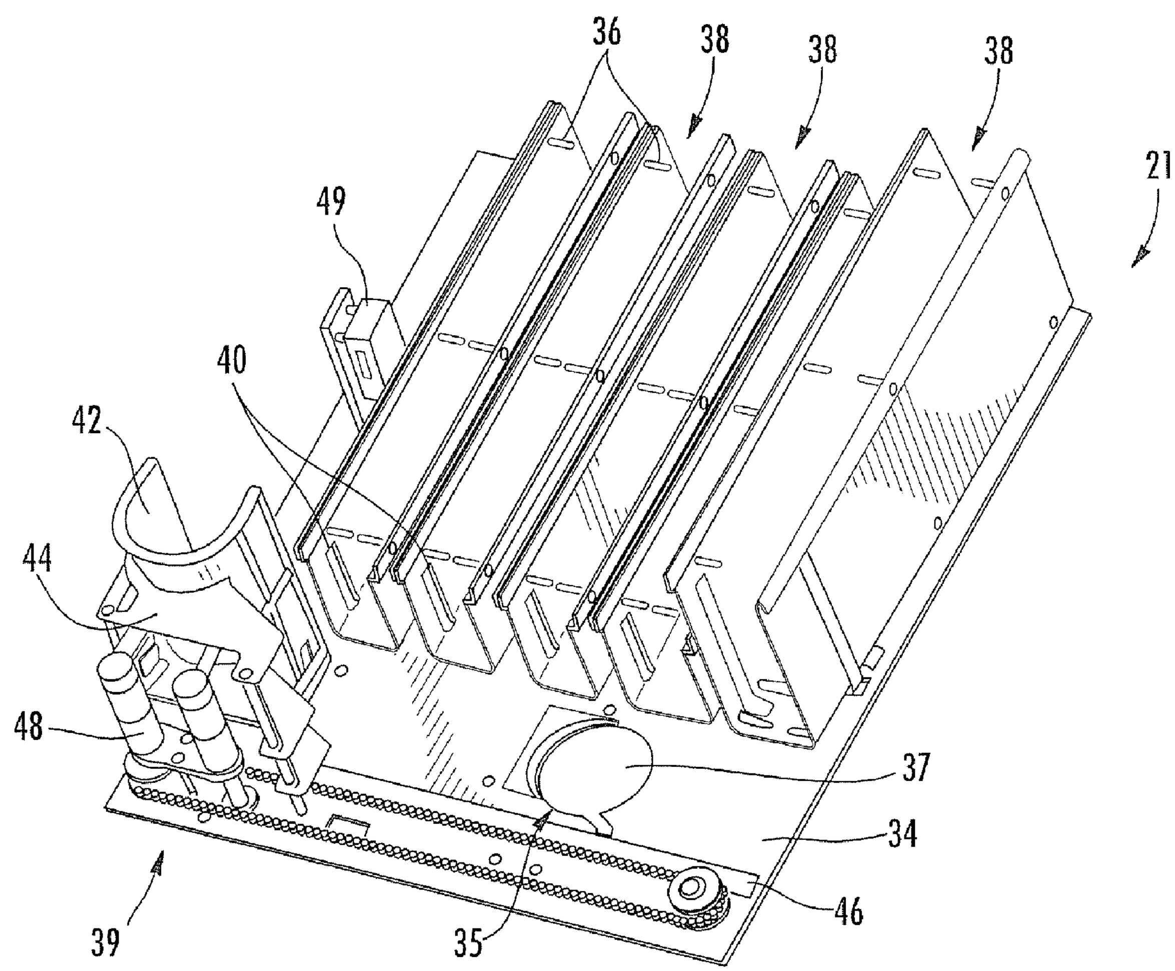
FIG. 4 is a right front perspective view of the vial loading station and the bar code scanning station of the pharmaceutical verification system of FIG. 2.
Figure 5:
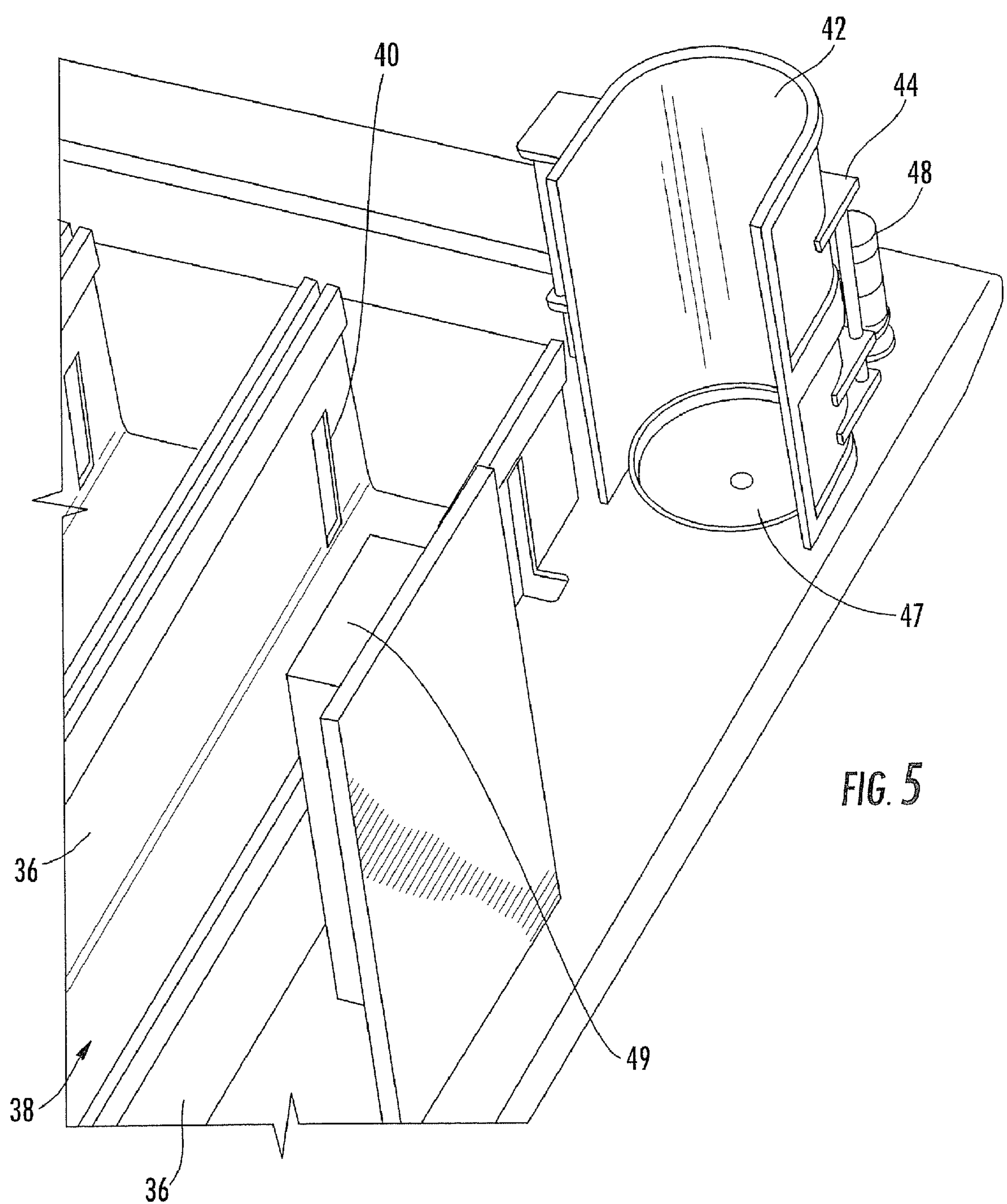
FIG. 5 is an enlarged rear perspective view of the bar code scanning station of FIG. 4.

Turning now to FIGS. 3-5, the vial loading station 21 is mounted on top of the ceiling 304. The vial loading station 21 includes a sloping ramp 34 on which are mounted a set of dividers 36. The ramp 34 is supported from underneath by a scaffold 33 and a wedge-shaped block 31. The dividers 36 define a series of parallel lanes 38 that terminate at a lower region of the ramp 34. In some embodiments, the dividers 36 are sized and positioned to form lanes 38 of different heights and/or widths. At the lower end of each lane 38, a retractable stop 40 extends into the lane 38 to prevent the undetained passage of vials. Each lane 38 may also include a sensor (not shown) to detect the presence of a vial. An exit hole 35 is located on the ramp below the ends of the lanes 38; a spring-loaded retractable cover 37 covers the exit hole 35.

Just beyond the lower ends of the lanes 38, the sliding conveyor 39 is located and includes a semicylindrical holder 42 mounted on a slide frame 44 with its open side facing the lanes 38. The slide frame 44 is in turn mounted on a rail 46 that extends perpendicular to the direction of the lanes 38. A drive mechanism 48 is mounted to the slide frame 44 to drive the slide frame 44 and the holder 42 along the rail 46.

The bar code scanning station 22 includes a bar code scanner 49 mounted adjacent to and beside an outermost divider 36. The bar code scanner 49 is oriented to scan a vial positioned within the holder 42 when the holder 42 is moved outside of the outermost divider 36 (i.e., near the side wall 305). A small turntable 47 driven by a motor and belt (not shown, and mounted under the ramp 34) is positioned between the bar code scanner 49 and the rail 46.

In operation, the lanes 38 are loaded at their upper ends with labeled, filled, capped pharmaceutical vials. The vials may be loaded by hand, or may be loaded with a robotic arm, such as the carriers of the automated pharmaceutical dispensing machines discussed in U.S. patent application Ser. No. 11/599,526, filed Nov. 14, 2006, and U.S. patent application Ser. No. 12/014,285, filed Jan. 15, 2008, the disclosures of which are hereby incorporated herein. The controller 200 determines from which lane 38 a loaded vial is to be released and actuates the drive mechanism 48 of the sliding conveyor 39 to slide the holder 42 into position at the end of the designated lane 38. The controller 200 then signals the stop 40 in that lane 38 to retract, thereby enabling the vial to slide down the ramp 34 and into the holder 42. Once the vial has reached the holder 42, the controller 200 signals the drive mechanism 48 of the sliding conveyor 39 to slide the holder 42 and vial to the far end of the rail 46 to a position upon the turntable 47 in front of the bar code scanner 49. The controller 200 signals the turntable motor to rotate the turntable 47. The bar code scanner 49 reads the bar code on the vial and stores information contained therein, including the identity of the prescribed pharmaceutical (or a pharmacy/prescription code that indirectly identifies the pharmaceutical), in memory accessible to the controller 200.

Those skilled in this art will appreciate that other techniques of reading information about the expected pharmaceutical from a vial, such as RFID, may also be employed. The turntable 47 may also be omitted in some embodiments.

Also, the conveyor lanes 38 are not required; in some embodiments a technician may commence operations by simply placing a vial in position for scanning. Further, the conveyor may be configured as a belt conveyor, a robotic arm, or the like as desired. In other embodiments, a suction tube-type delivery unit, in which vials are conveyed to and from the system 20 via tubes to which suction is applied, may be employed in place of or in conjunction with the loading station 21 and/or the offloading station 30.

Once scanning is complete, the controller 200 signals the drive mechanism 48 of the sliding conveyor 39 to slide the holder 42 and vial along the rail 46 to the exit hole 35. The cover 37 is configured such that a vial sliding away from the bar code scanner 49 forces the cover 37 away from the exit hole 35 (for example, the cover 37 may be spring-loaded toward its closed position, with a stepped ramp that catches on the bottom edge of a vial traveling away from the bar code scanner 49). As a result, the vial drops through the exit hole 35, through a tube 50 positioned between the ramp 34 and the ceiling 304, and into a recess 110 of the wheel conveyer 32 as the recess 110 is positioned in the vision station 24 (FIG. 6).

Figure 6:
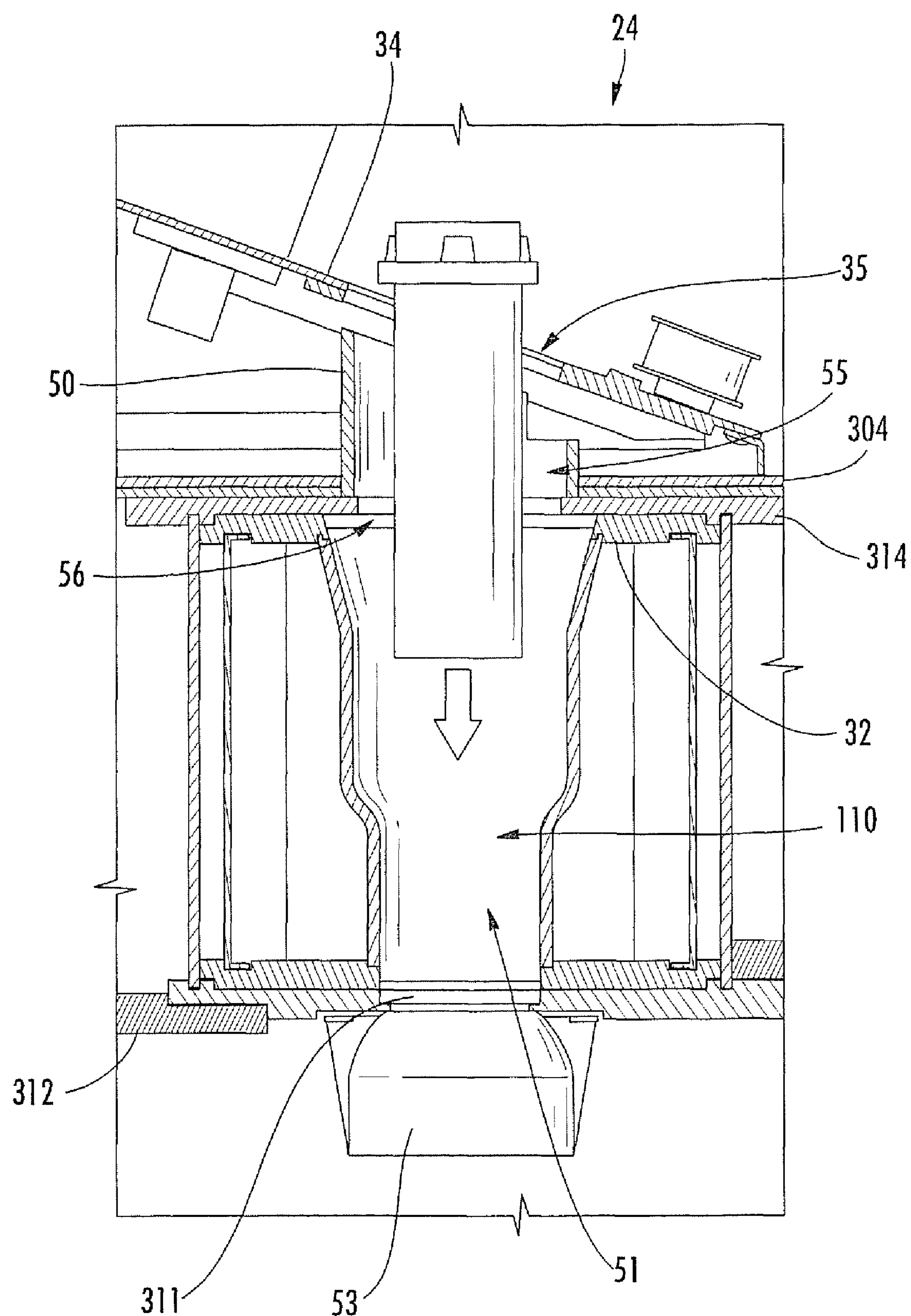
FIG. 6 is an enlarged side section view of the vision station of the pharmaceutical verification system of FIG. 2 showing a vial entering the vision chamber.

Referring now to FIGS. 6-8, the wheel conveyor 32 is generally a round wheel or carousel with four substantially identical open-sided recesses 110 located approximately 90 degrees apart. Each of the recesses 110 is flared outwardly at its top edges to encourage dropping vials to descend to the bottom of the recess 110 and is open at its bottom end. The wheel conveyor 32 is rotatably mounted on the shelf 312 for rotation about an axis A1. A motor (not shown) is attached to the wheel conveyor 32 and mounted under the shelf 312 and is configured to drive the wheel conveyor 32 about the axis A1 according to signals from the controller 200.

The illustrated wheel conveyor 32 has four recesses 110, but other numbers of recesses may be suitable. Also, other types of conveyors, such as belt conveyors and robotic arms, may be employed to move the vial between stations.

The recess 110, the shelf 312 and the shelf 314 combine to form a chamber 51 of the vision station 24. The shelf 312 includes a window 311 (typically covered with glass, which may be tinted) that provides visual access to the chamber 51 from underneath.

Turning to FIGS. 6 and 8, a camera 52 is mounted on the shelf 310 and positioned to acquire an image through the window 311. A light dome 53 is positioned between the camera 52 and the window 311. A light ring 54 is mounted to the lower rim of the light dome 53 to provide light to the chamber 51. In some embodiments, the light ring 54 includes adjustable RGB lighting capability, such that the color of light emitted by the light ring 54 can be adjusted as desired. Additional detail regarding the vision station is set forth in co-pending and co-assigned U.S. Provisional Patent Application Ser. No. 61/118,014, filed Nov. 26, 2008, and U.S. patent application Ser. No. 12/623,878, filed concurrently and entitled System and Method for Acquiring Images, the disclosure of each of which is hereby incorporated herein in its entirety.

In operation, a vial drops into the chamber 51 through the exit hole 35, the tube 50, and through holes 55, 56 in the ceiling 304 and shelf 314, respectively. The shape of the recess 110 urges the vial to the bottom of the chamber 51 (formed by the shelf 312 and the window 311), where it rests with its bottom end on the window 311. The controller 200 activates the camera 52 to acquire one or more images of the pharmaceuticals in the vial, typically while illuminated by the light ring 54. In some embodiments, the chamber 51 or the vial may be illuminated with a colored light that is substantially the "inverse" of the color of the vial, as such illumination may improve the quality of the image of the pharmaceuticals; this technique is discussed in co-pending and co-assigned U.S. patent application Ser. No. 12/249,402, filed Oct. 10, 2008, the disclosure of which is hereby incorporated herein in its entirety. The images taken by the camera 52 can then be stored in memory accessible by the controller 200 and/or compared to stored images of the prescribed pharmaceutical to assist in the verification process. It should be noted that the vision station 24 is designed to attempt to control, preferably to reduce or minimize, the amount of external or ambient light reaching the chamber 51 in order to improve the quality and consistency of images acquired therein.

Those skilled in this art will recognize that other configurations for the vision station may be employed. For example, the vision station may use white light and/or may use direct or indirect light to illuminate the vial. The vision station may also use infrared light for illumination and/or may be designed to illuminate the vial from other angles. Also, video or still images may be acquired. The vision station may include features that maintain the vial above the window 311 in order to avoid scratching the glass, and/or the vision station may be modified such that the vial does not drop directly onto the window 311.

Figure 9:
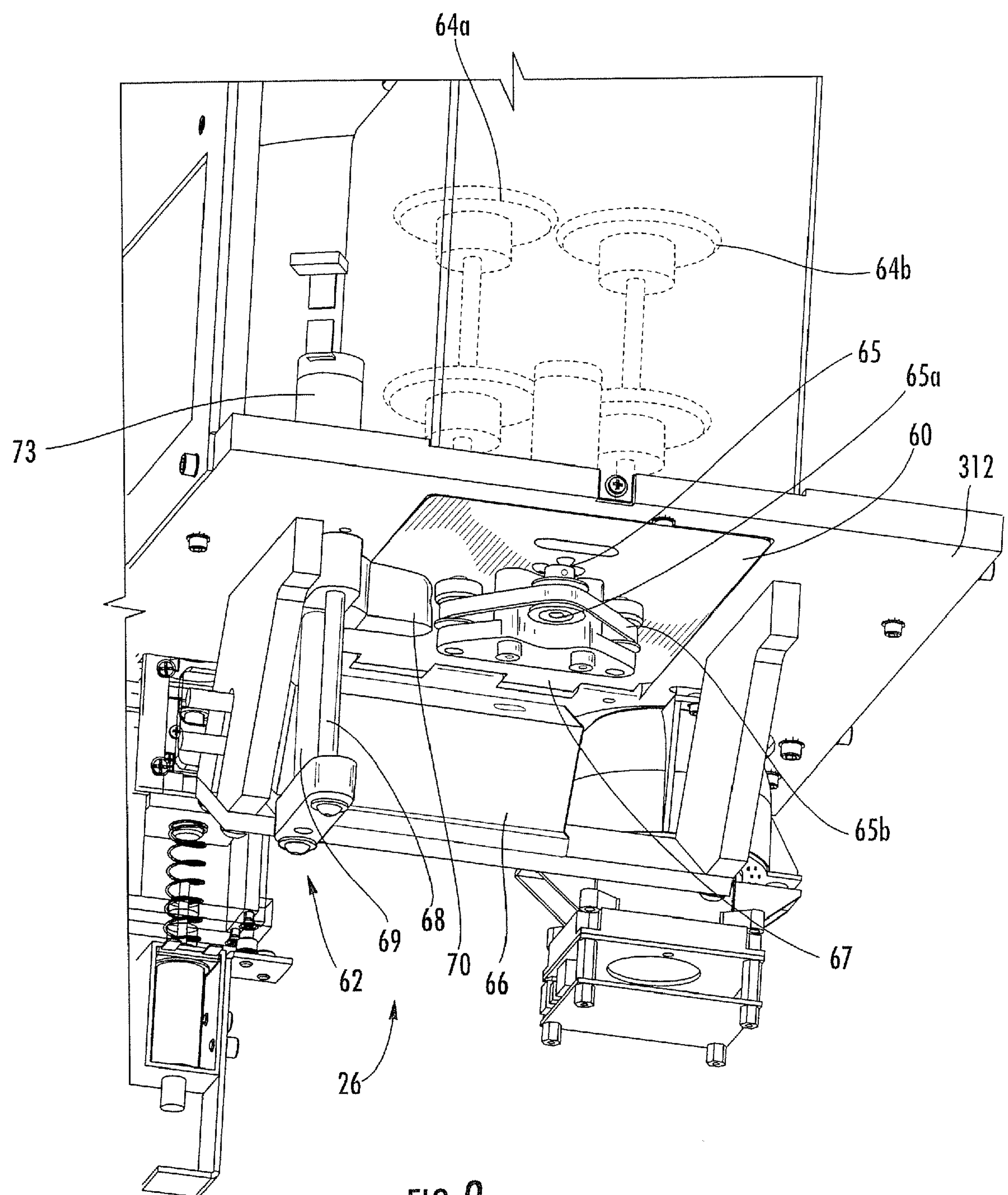
FIG. 9 is a bottom, left, front perspective view of the spectroscopy station of the pharmaceutical verification system of FIG. 2, with the floor section in its level position.
Figure 10:
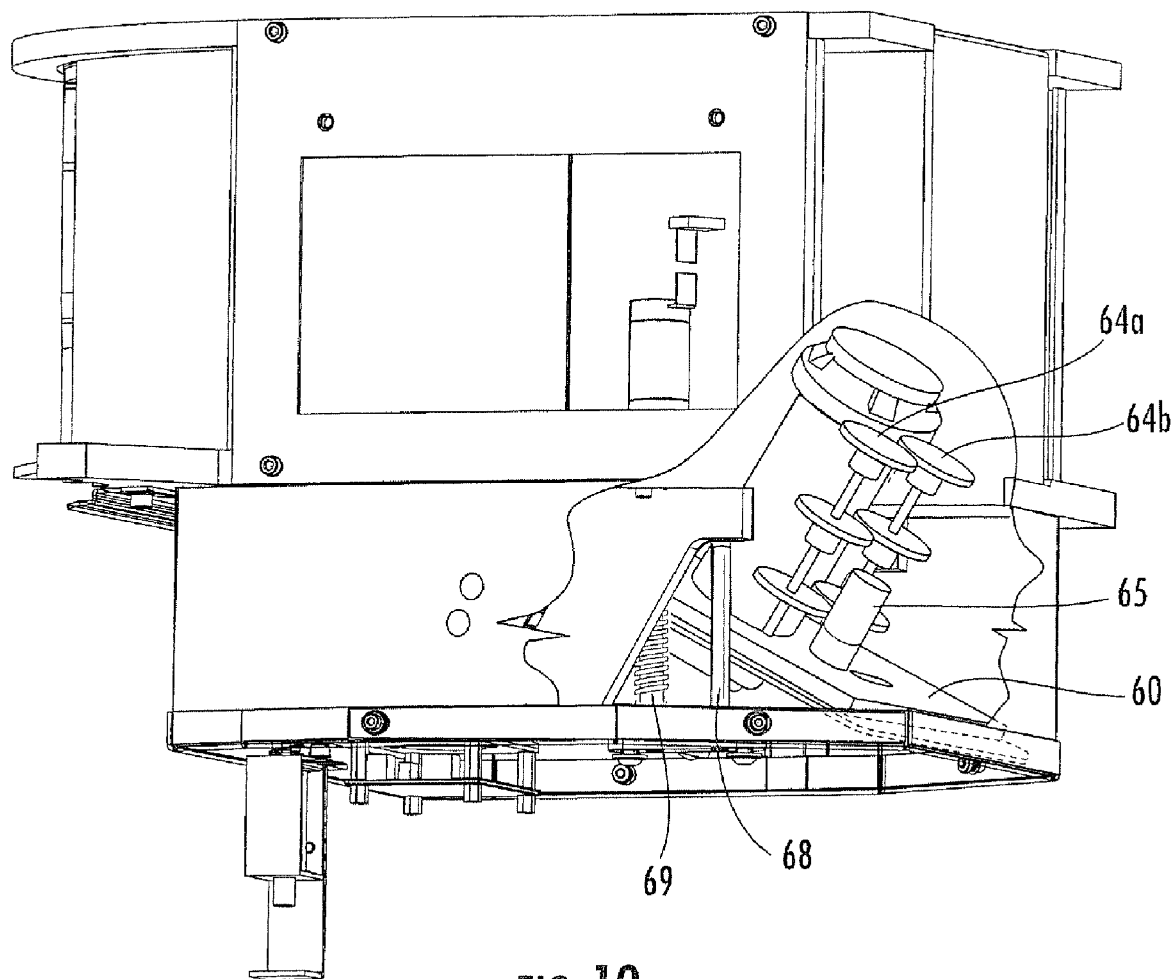
FIG. 10 is a bottom, left, front perspective view of the spectroscopy station of the pharmaceutical verification system of FIG. 2, with the floor section in its tilted position.

Turning now to FIGS. 9 and 10, once one or more images of the vial have been taken with the camera 52, the controller 200 signals the wheel conveyor motor to rotate the wheel conveyor 32 90 degrees (this rotation is clockwise from the vantage point of FIG. 7), which slides the vial on the shelf 312 and positions the vial in the spectroscopy station 26. The spectroscopy station 26 includes a pivoting floor section 60 that includes an open window (not shown). The floor section 60 is attached to the shelf 312 at a pivot 67 located near the axis A1. Two rollers 64*a*, 64*b* are mounted on the floor section 60 for rotation about axes of rotation that are generally normal to the floor section 60, and driven by a drive motor 65 via a belt pulley 65*a* and a belt 65*b* that are mounted to the underside of the floor section 60.

A tilt mechanism 62 is attached to the shelf 312 to move the floor section 60 to move it between a level position, in which the floor section 60 is substantially coplanar with the shelf 312 (FIG. 9), and a tilted position, in which the floor section 60 rotates about the pivot 67 to lowers its opposite edge (FIG. 10). The tilt mechanism 62 includes a vertical guide shaft 68 that extends between the shelves 310, 312, an acme screw 69 that also extends between the shelves 310, 312, and a supporting follower 70 that is threaded onto the acme screw 69. The supporting follower 70 supports the floor section 60 from underneath. A motor 73 mounted on the upper surface of the shelf 312 drives the acme screw 69.

The spectroscopy station 26 includes a spectroscopic probe 66 that is positioned below the shelf 312. An exemplary configuration for the spectrometer and probe 66 is described in U.S. patent application Ser. No. 11/972,849, supra. The spectroscopic probe 66 is oriented to shine a laser beam through the window (not shown) in the floor section 60 when the floor section 60 is in its tilted position.

In operation, once the wheel conveyer 32 has rotated the vial to the spectroscopy station 26, the controller 200 signals the tilt mechanism 62 to lower the floor section 60 from the level position to the tilted position. To do so, the acme screw motor 73 rotates the acme screw 69 so that the supporting follower 70 descends. The floor section 60 descends with the supporting follower 70 as it pivots about the pivot 67. In the tilted position (FIG. 10), the vial rests against the rollers 64*a*, 64*b*. The controller 200 then signals the spectroscopic probe 66 to acquire one or more spectra of the pharmaceuticals in the vial. Before or as spectral data is being collected and analyzed, the motor 65 drives the belt pulley 65*a*, which in turn drives the belt 65*b*. Movement of the belt 65*b* rotates the rollers 64*a*, 64*b*, which in turn rotates the vial. Such rotation can assist the pills in "settling" in the vial and provide multiple "views" of the vial to the spectroscopic probe 66, which can enable the controller 200 to select the view that provides the more accurate reading(s) and/or can reduce the heating effect of the spectroscopic laser on the sample and the vial. The spectral data can then be stored in memory accessible to the controller 200 and/or compared to stored spectral data to determine whether the dispensed pharmaceutical matches the prescribed pharmaceutical. It should be noted that the spectroscopic station 26 is designed to attempt to control, preferably to reduce or minimize, the amount of external or ambient light reaching the vial in order to improve the quality and consistency of spectral data acquired therein.

In some embodiments, the spectroscope is a Raman spectrometer; in other embodiments, other spectroscopic techniques, such as IR, near-IR, or ultraviolet, may be employed. The spectroscopy station may employ a non-pivoting floor, a non-tilting floor and/or rollers to rotate the vial, or may have other mechanisms to tilt and/or rotate the vial.

Figure 11:
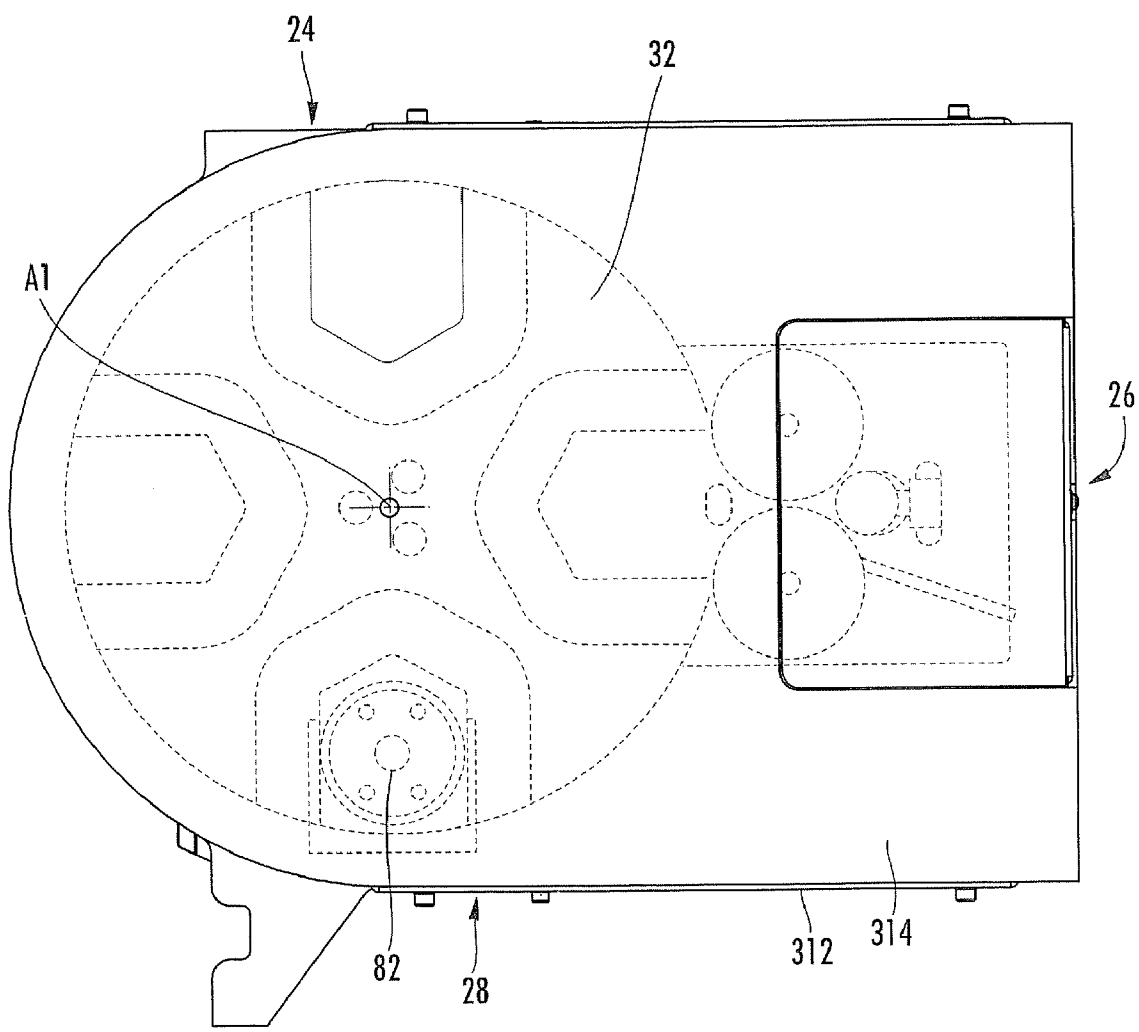
FIG. 11 is a top view of the vision, spectroscopy and stamping stations of the pharmaceutical verification system of FIG. 2, showing a vial being stamped for approval.

Once the spectroscopic scanning is complete, the controller 200 signals the tilt mechanism 62 to raise the floor section 60 back to the level position (FIG. 9). The controller 200 then signals the motor (not shown) to rotate the wheel conveyor 32 90 degrees to move the vial to the stamping station 28 (FIG. 11). If the procedures followed in the vision and spectroscopy stations 24, 26 indicate that the dispensed pharmaceutical matches the prescribed pharmaceutical, the controller 200 then signals a stamping device 82 in the stamping station 28 mounted under the shelf 312 to mark the vial (typically on the bottom of the vial) with indicia of verification. If instead the prescribed and dispensed pharmaceuticals are not deemed to match, the controller 200 does not signal the stamping device 82 to mark the vial (similarly, the stamping device 82 does not mark the vial if approval is withheld for another reason, such as the prescribed pharmaceutical not being included in the memory of the controller 200, thereby precluding analysis of the prescription). Procedures for determining whether the identities of the dispensed and prescribed pharmaceuticals match are described in co-pending and co-assigned U.S. Provisional Patent Application Ser. No. 61/118,011, filed Nov. 26, 2009, and, U.S. patent application Ser. No. 12/623,822, filed concurrently, the disclosure of each of which is hereby incorporated herein by reference in its entirety. In some embodiments, a UV-sensitive dye or the like may be used to stamp the vial to avoid copying. Also, in embodiments in which the label of the vial is marked, a UV-sensitive ink or the like may be employed to avoid interference with other information on the label. Those skilled in this art will appreciate that other means of approving the vial, such as printing on the label or the vial, lasing a mark on the vial, or writing to an RFID tag, may also be employed at an approval station, or the approval station may be omitted entirely in some embodiments.

Figure 12:
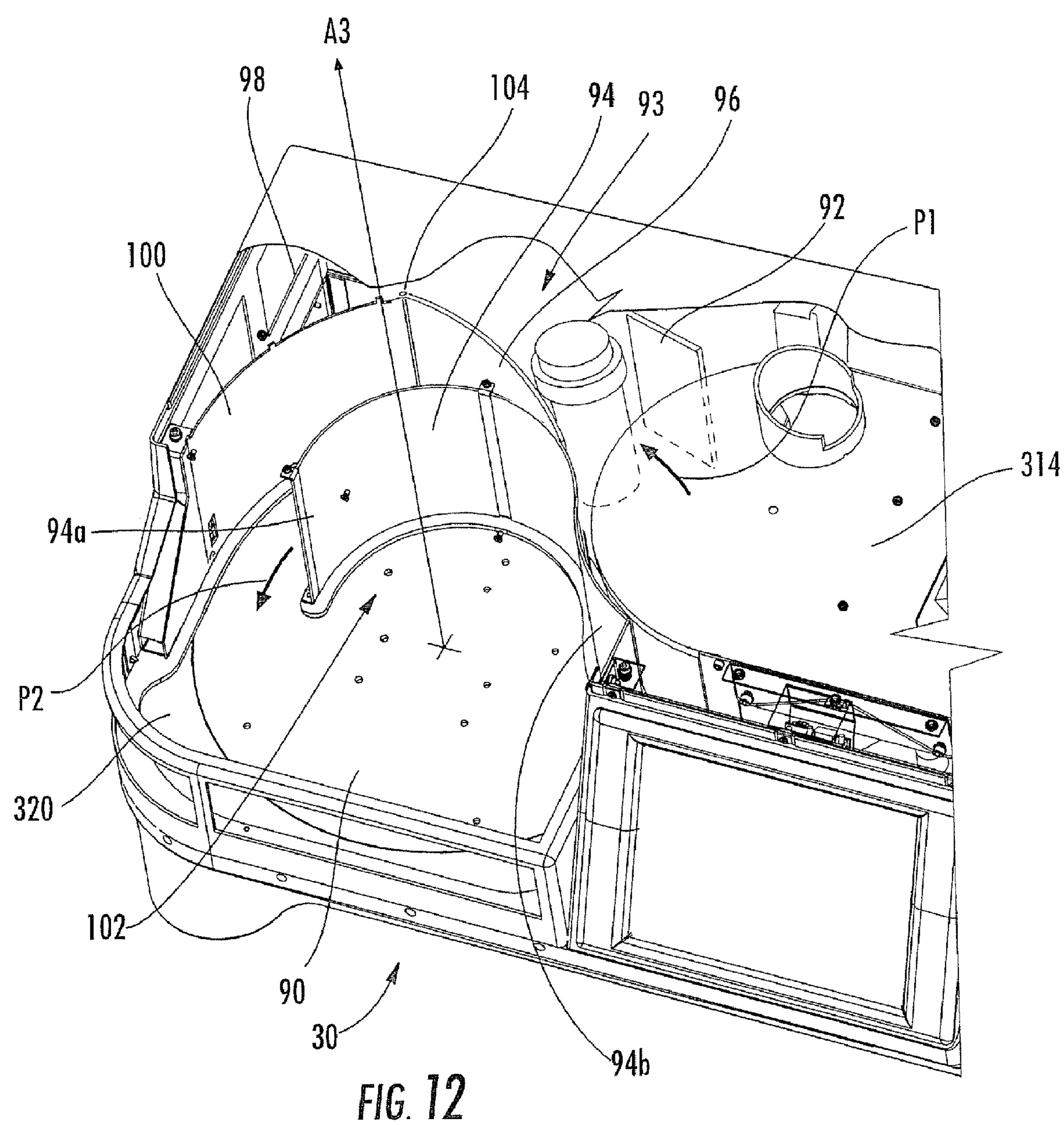
FIG. 12 is a top, left perspective view of the offload station of the pharmaceutical verification system of FIG. 2, with the gate of the offload station shown in its closed position; the bar code scanning station and ceiling have been removed.
Figure 13:
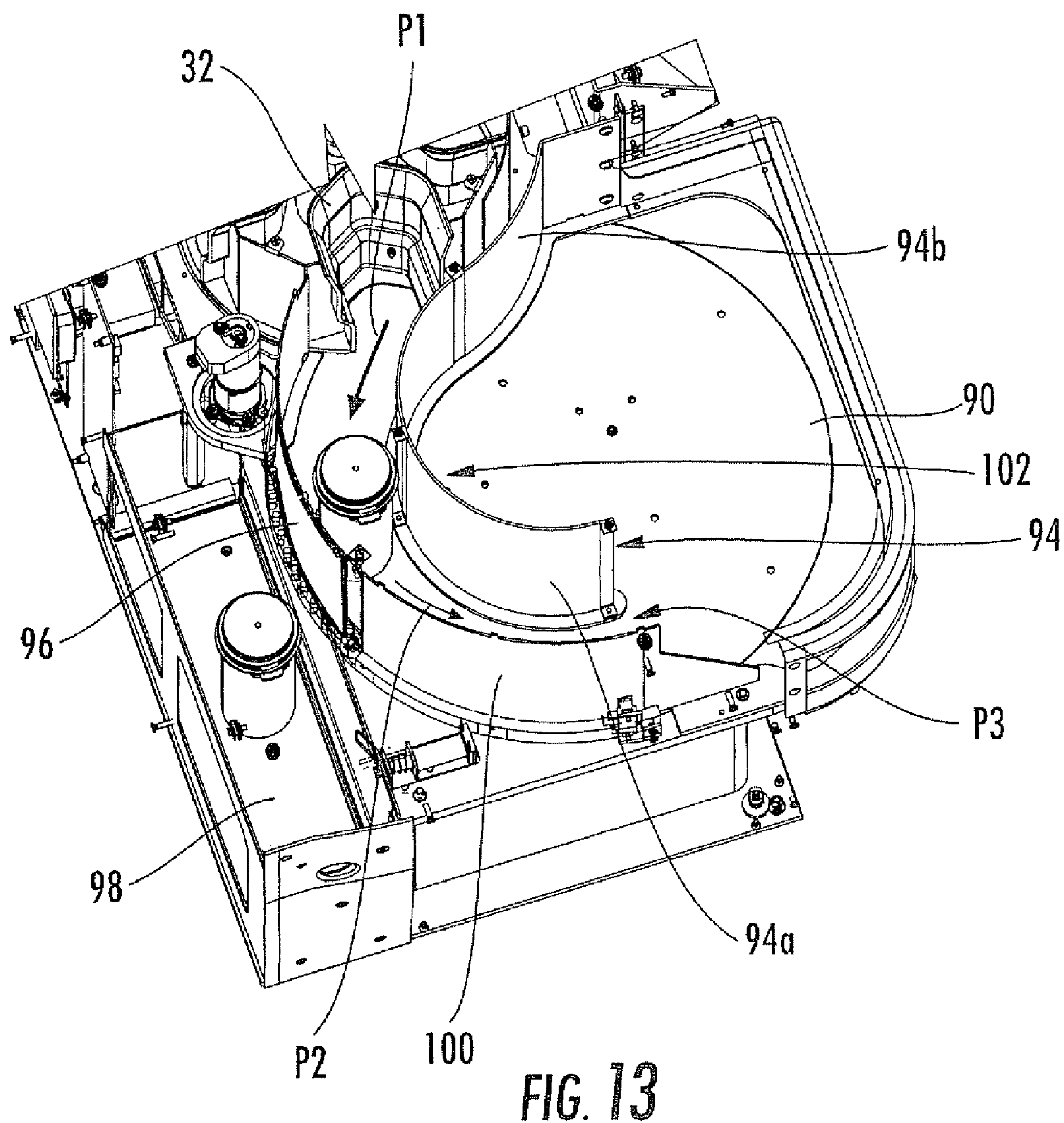
FIG. 13 is a top, rear, right perspective view of the offload station of FIG. 12 showing the gate in its open position.

After operations in the stamping station 28 are complete, the controller 200 signals the wheel conveyor motor to rotate the wheel conveyor 32 another 90 degrees to the offload station 30 (FIGS. 12 and 13). The offload station 30 includes a turntable 90 that is mounted within an opening in a platform 320 that is generally coplanar with the shelf 312; the turntable 90 is mounted to rotate about an axis of rotation A3. One section of the turntable 90 underlies the recess 110 of the wheel conveyor 32 as that recess 110 is positioned in an offloading position (i.e., 90 degrees from each of the vision and stamping stations 24, 28). A motor is mounted under the platform 320 to drive the turntable 90 about the axis A3. An outer guide 92 is mounted on the platform 320 over a portion of the perimeter of the turntable 90 between the offload position and the vision station 24. A gap 93 between the outer guide 92 and outer wall 100 leads to an exception area 98. An inner wall 94 is mounted to the platform 320 such that a travel path segment P1 is formed on the turntable 90 between the inner wall 94 and the outer guide 92. The inner wall 94 has a generally semicircular portion 94*a* and a separate arcuate portion 94*b*. The outer wall 100 is mounted to the platform 320 over approximately 70 degrees of the perimeter of the turntable 90. A travel path segment P2 is defined between the outer wall 100 and much of the semicircular portion of the inner wall 94, such that together the segments P1, P2 form a travel path P3. A gate 96 is pivotally attached at a pivot 104 to the end of the outer wall 100 nearest the outer guide. The interior of the semicircular portion 94*a* forms a collection area 102 that is generally concentric with the turntable 90.

In operation, the gate 96 begins in a closed position (FIG. 12), in which it separates the path segments P1, P2 of the travel path P3 and leaves open the gap 93 between the outer guide 92 and outer wall 100. If the operations performed by the vision station 24 and/or the spectroscopic station 26 determine that verification of the dispensed pharmaceutical as the prescribed pharmaceutical cannot be achieved, the controller 200 instructs the gate 96 to remain in the closed position. As the wheel conveyor 32 rotates the vial to a position over a segment of the turntable 90, it deposits the vial along the path segment P1 onto the turntable 90. Rotation of the turntable 90 (counterclockwise from the vantage point of FIG. 12) then conveys the vial to and through the gap 93 and into the exception area 98, where it can be removed by a technician.

If instead the operations performed by the vision station 24 and the spectroscopic station 26 verify that the dispensed pharmaceutical is the prescribed pharmaceutical, the controller 200 instructs the gate 96 to move to an open position (FIG. 13), in which the gate 96 covers the gap 93. The vial can then follow path segments P1 and P2 between the inner and outer walls 94, 100. Continued rotation conveys the vial to the surface of the arcuate portion 94*b* of the inner wall 94 opposite the wheel conveyor 32, then to the pocket 102. The verified vial can then be retrieved from the pocket 102.

Those skilled in this art will recognize that other configurations for offloading vials may be suitable for use with the present invention. For example, some offload stations may not physically separate approved and exception vials, but instead may rely on visual indicia on the vial to notify a technician of exceptions. Some embodiments may employ lanes, chutes or suction tubes rather than a turntable to separate exceptions and/or to offload vials. Other configurations will be apparent to those of skill in this art.

Figure 14:
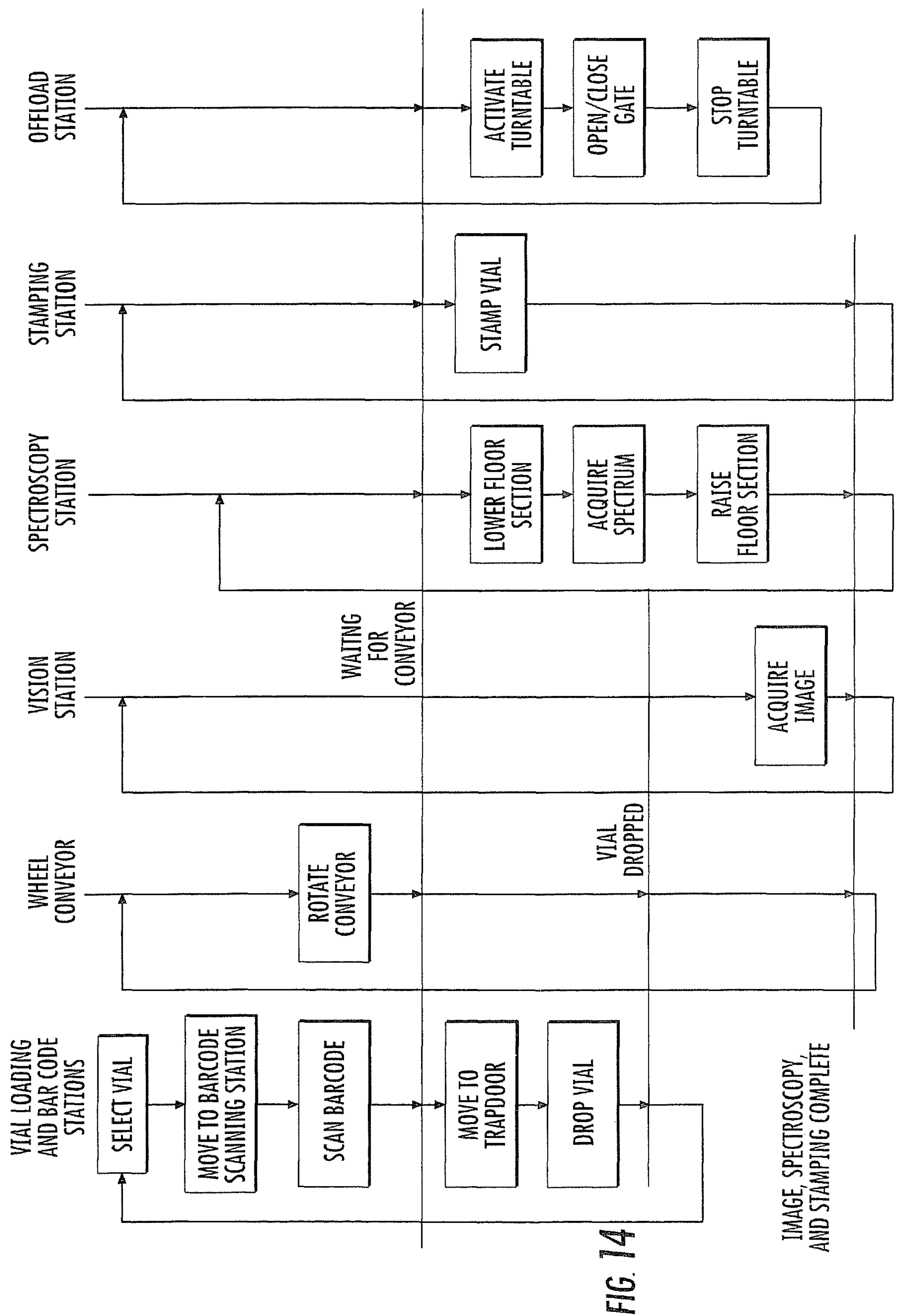
FIG. 14 is a concurrency diagram illustrating the sequence and concurrency of operational steps according to embodiments of the invention.

Referring now to FIG. 14, the sequence and concurrency of operations are shown therein. As can be seen in FIG. 14, the vision, spectroscopy and stamping stations 24, 26, 28 are idle as the sliding conveyor 39 moves the vial from the vial loading station 21 to a position in front of the bar code scanner 49. As the bar code is scanned, the wheel conveyor 32 rotates 90 degrees. Once the wheel conveyor 32 has rotated, the sliding conveyor 39 moves the vial to the opening 35, moving the door 37 to an open position while doing so. Simultaneously, the floor section 61 of the spectroscopy station 26 is lowered, the stamping device 82 stamps a vial in the stamping station 28, and the turntable 90 is activated and begins to rotate. As the scanned vial drops through the opening 35 and into the vision chamber 51, the spectroscopic probe 66 acquires a spectrum of a vial, and the gate 93 moves to its open or closed position (if necessary). After the vial drops into the vision chamber, an image is taken in the vision station 24, the floor section 61 is raised to its level position, and the turntable 90 ceases its rotation. At this point the imaging, spectroscopy, and stamping steps are complete, and a previously stamped vial has been offloaded. The process is then repeated when another vial is scanned in the bar code scanning station 22. Software for the controller 200 that enables it to control operation of the system 20 is described in co-pending and co-assigned U.S. Provisional Patent Application No. 61/118,011 and U.S. patent application Ser. No. 12/623,822, supra Those of skill in this art will understand that the afore-described sequence/concurrence of steps is exemplary of one embodiment only, and may be varied for other embodiments of the invention, particularly if some stations are omitted, more or fewer recesses are present in the wheel conveyor, and/or other types of conveyors are employed.

The foregoing is illustrative of the present invention and is not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. The following claims are provided to ensure that the present application meets all statutory requirements as a priority application in all jurisdictions and shall not be construed as setting forth the scope of the invention.

That which is claimed is:

1. A method of confirming the identity of the contents of pharmaceutical vials, comprising the steps of:

(a) scanning a bar code on a first vial to determine the expected contents of the first vial;
(b) conveying the first vial to a vision station;
(c) acquiring an image of the contents of the first vial at the vision station;
(d) scanning a bar code on a second vial to determine the expected contents of the second vial;
(e) conveying the first vial to a spectroscopy station;
(f) conveying the second vial to the vision station;
(g) acquiring an image of the contents of the second vial at the vision station;
(h) acquiring a spectrum of the contents of the first vial at the spectroscopy station;
(i) scanning a bar code on a third vial to determine the expected contents of the third vial;
(j) conveying the first vial to an approval station;
(k) conveying the second vial to the spectroscopy station;
(l) conveying the third vial to the vision station;
(m) acquiring an image of the contents of the third vial at the vision station;
(n) acquiring a spectrum of the contents of the second vial at the spectroscopy station;
(o) determining, based on at least one of steps (c) and (h), whether the contents of the first vial match the expected contents of the first vial and, if so, affixing indicia of approval on the first vial at the approval station;
(p) scanning a bar code on a fourth vial to determine the expected contents of the fourth vial;
(q) conveying the first vial to an offload station;
(r) conveying the second vial to the approval station;
(s) conveying the third vial to the spectroscopy station; and
(t) conveying the fourth vial to the vision station.

2. The method defined in claim 1, wherein the conveying of the first, second and third vials in steps (q), (r) and (s) is performed simultaneously.

3. The method defined in claim 2, wherein the conveying of the first, second and third vials in steps (q), (r) and (s) is performed with a single conveyor.

4. The method defined in claim 3, wherein the single conveyor is a rotatable wheel.

5. The method defined in claim 1, wherein steps (b), (f), (l) and t) are performed with a first conveyor, and wherein the remaining conveying steps are performed with a second, different conveyor.

* * * * *